United States Patent [19]
Bandman et al.

[11] Patent Number: 5,853,997
[45] Date of Patent: Dec. 29, 1998

[54] HUMAN PROTEIN PHOSPHATASE

[75] Inventors: Olga Bandman, Mountain View; Surya K. Goli; Preeti Lal, both of Sunnyvale; Neil C. Corley, Mountain View; Hong Zhang, Pleasant Hills, all of Calif.

[73] Assignee: Incyte Pharmaceuticals, Inc., Palo Alto, Calif.

[21] Appl. No.: 873,093

[22] Filed: Jun. 11, 1997

[51] Int. Cl.$^6$ ............... C12N 9/16; C12N 1/20; C12Q 1/68; C07H 21/04
[52] U.S. Cl. ............ 435/6; 435/196; 435/252.3; 435/254.11; 435/320.1; 435/325; 435/410; 536/23.2; 935/22
[58] Field of Search ............ 435/6, 196, 320.1, 435/252.3, 254.11, 325, 410; 536/23.2; 935/22

[56] References Cited

PUBLICATIONS

Charbonneau, H. et al., "1002 Protein Phosphatases?", *Annu. Rev. Cell Biol.*, 8: 463–493 (1992).
Wenk, J. et al., "Molecular cloning and primary structure of a protein phosphatase 2C isoform", *FEBS Lett.*, 297: 135–138 (1992).
Terasawa, T. et al., "Molecular Cloning of a Novel Isotype of $Mg^{2+}$–Dependent Protein Phosphatase β (Type 2Cβ) Enriched in Brain and Heart", *Arch. Biochem. Biophys.*, 307: 342–349 (1993).
Kato, S. et al., "Molecular Cloning and Expression of Mouse $Mg^{2+}$–Dependent Protein Phosphatase β–4 (Type 2Cβ–4)", *Arch. Biochem. Biophys.*, 318: 387–393 (1995).
Wenk, J., et al., (Direct Submission), GenBank Sequence Database (Accession 247927), National Center for Biotechnology Information, National Library of Medicine, Bethesda, Maryland, 20894 (GI 247927).
Wenk, J., et al., (Direct Submission), GenBank Sequence Database (Accession S90449), National Center for Biotechnology Information, National Library of Medicine, Bethesda, Maryland, 20894 (GI 247926).
Terasawa, T., et al., (Direct Submission), GenBank Sequence Database (Accession 452526), National Center for Biotechnology Information, National Library of Medicine, Bethesda, Maryland, 20894 (GI 452526).
Terasawa, T., et al., (Direct Submission), GenBank Sequence Database (Accession D17411), National Center for Biotechnology Information, National Library of Medicine, Bethesda, Maryland, 20894 (GI 452525).

*Primary Examiner*—Robert A. Wax
*Assistant Examiner*—Einar Stole
*Attorney, Agent, or Firm*—Sheela Mohan-Peterson; Lucy J. Billings; Incyte Pharmaceuticals, Inc.

[57] ABSTRACT

The invention provides a human protein phosphatase (PROPHO) and polynucleotides which identify and encode PROPHO. The invention also provides expression vectors, host cells, agonists, antibodies and antagonists. The invention also provides methods for treating disorders associated with expression of PROPHO.

11 Claims, 11 Drawing Sheets

```
          9          18          27          36          45          54
NNA TAT TGT ACC TAT CAG GCG TCA GCT CTC AAT CTA GAT CCC TCC CTG GCC TCG 63          72          81          90          99         108
GAC TTA TTG CAA AAC ATG GGT GCT TTT TTG GAT AAA CCC AAA ACT GAA AAA CAT
                         M   G   A   F   L   D   K   P   K   T   E   K   H 117         126         135         144         153         162
AAT GCT CAT GGT GCT ATG GGG AAT GGT TTA CGT TAT GGC CTG AGC ATG CAA GGA
 N   A   H   G   A   M   G   N   G   L   R   Y   G   L   S   M   Q   G 171         180         189         198         207         216
TGG AGA GTG GAA ATG GAA GAT GCA CAC ACA GCT GTT GTA GGT ATT CCT CAC GGC
 W   R   V   E   M   E   D   A   H   T   A   V   V   G   I   P   H   G 225         234         243         252         261         270
TTG GAA GAC TGG TCA TTT TTT GCA GTT TAT GAT GGT CAT GCT GGA TCC CGA GTG
 L   E   D   W   S   F   F   A   V   Y   D   G   H   A   G   S   R   V 279         288         297         306         315         324
GCA AAT TAC TGC TCA ACA CAT TTA GAA CAC TTA TTA GAG CAT ATC ACT ACT AAC GAA GAC TTT
 A   N   Y   C   S   T   H   L   E   H   L   L   E   H   I   T   T   N   E   D   F 333         342         351         360         369         378
AGG GCA GCT GGA AAA TCA GGA TCT GCT CTT GAG CTT TCA GTG GAA AAT GTT AAG
 R   A   A   G   K   S   G   S   A   L   E   L   S   V   E   N   V   K
```

```
387         396         405         414         423         432
AAT GGT ATC AGA ACT GGA TTT TTG AAA ATT GAT GAA TAC ATG CGT AAC TTT TCA
 N   G   I   R   T   G   F   L   K   I   D   E   Y   M   R   N   F   S 441         450         459         468         477         486
GAC CTC AGA AAC GGG ATG GAC AGG ATC TAC TTT ATC AGT GGA ACT GCA GTG GGA GTT ATG ATT
 D   L   R   N   G   M   D   R   I   Y   F   I   S   G   T   A   V   G   V   M   I 495         504         513         522         531         540
TCA CCT AAG CAT ATC TAC TTT ATC AAC TGT GGT GAT TCA CGT GCT GTT CTG TAT
 S   P   K   H   I   Y   F   I   N   C   G   D   S   R   A   V   L   Y 549         558         567         576         585         594
AGG AAT GGA CAA GTC ATC TGC TTT TCT ACC CAG GAT CAC AAA CCT GCT AAT CCA AGG
 R   N   G   Q   V   I   C   F   S   T   Q   D   H   K   P   A   N   P   R 603         612         621         630         639         648
GAA AAG GAG CGA ATC CAA AAT GCA GGA GGC AGC GTG ATG ATA CAA CGT GTT AAT
 E   K   E   R   I   Q   N   A   G   G   S   V   M   I   Q   R   V   N 657         666         675         684         693         702
GGT TCA TTA GCA GTA TCT CGT GCT CTG GGG GAC TAT GAT TAC AAG TGT GTT GAT
 G   S   L   A   V   S   R   A   L   G   D   Y   D   Y   K   C   V   D 711         720         729         738         747         756
GGC AAG GGC CCA ACA GAA CAA CTT GTT TCT CCA GAG CCT GAG GTT TAT GAA ATT
 G   K   G   P   T   E   Q   L   V   S   P   E   P   E   V   Y   E   I
```

```
        765              774              783              792              801              810
TTA AGA GCA GAA GAG GAT GAA TTT ATC ATC TTG GCT TGT GAT GGG ATC TGG GAT
 L   R   A   E   E   D   E   F   I   I   L   A   C   D   G   I   W   D 819              828              837              846              855              864
GTT ATG AGT AAT GAG GAG CTC TGT GAA TAT GTT AAA TCT AGG CTT GAG GTA TCT
 V   M   S   N   E   E   L   C   E   Y   V   K   S   R   L   E   V   S 873              882              891              900              909              918
GAT GAC CTG GAA AAT GTG TGC AAT TGG GTA GTG GAC ACT TGT TTA CAC AAG GGA
 D   D   L   E   N   V   C   N   W   V   V   D   T   C   L   H   K   G 927              936              945              954              963              972
AGT CGA GAT AAC ATG AGT ATT GTA CTA GTT TGC TTT TCA AAT GCT CCC AAG GTC
 S   R   D   N   M   S   I   V   L   V   C   F   S   N   A   P   K   V 981              990              999             1008             1017             1026
TCA GAT GAA GCG GTG AAA AAA GAT TCA GAG TTG GAT AAG CAC TTG GAA TCA CGG
 S   D   E   A   V   K   K   D   S   E   L   D   K   H   L   E   S   R 1035             1044             1053             1062             1071             1080
GTT GAA GAG ATT ATG GAG AAG TCT GGC GAG GAA ATG CCT GAT CTT GCC CAT
 V   E   E   I   M   E   K   S   G   E   E   M   P   D   L   A   H 1089             1098             1107             1116             1125             1134
GTC ATG CGC ATC TTG TCT GCA GAA AAT ATC CCA AAT TTG CCT CCT GGG GGA GGT
 V   M   R   I   L   S   A   E   N   I   P   N   L   P   P   G   G   G
```

FIGURE 1C

```
      1143               1152               1161               1170               1179               1188
CTT GCT GGC AAG CGT AAT GTT ATT GAA GCT GTT TAT AGT AGA CTG AAT CCA CAT
 L   A   G   K   R   N   V   I   E   A   V   Y   S   R   L   N   P   H 1197               1206               1215               1224               1233               1242
AGA GAA AGT GAT GGG GCC TCC GAT GAA GCA GAG AGT GGA GAA TCA CAG GGA AAA
 R   E   S   D   G   A   S   D   E   A   E   S   G   E   S   Q   G   K 1251               1260               1269               1278               1287               1296
TTG GTG GAA GCT CTC AGG CAA ATG AGA ATT AAT CAT AGG GGA AAC TAC CGA CAA
 L   V   E   A   L   R   Q   M   R   I   N   H   R   G   N   Y   R   Q 1305               1314               1323               1332               1341               1350
CTT CTG GAG GAG ATG CTG ACT AGT TAC AGG CTA GCT AAA GTA GAG GGA GAA GAA
 L   L   E   E   M   L   T   S   Y   R   L   A   K   V   E   G   E   E 1359               1368               1377               1386               1395               1404
AGC CCT GCT GAA CCA GCT GCC ACA GCT ACT TCT TCG AAC AGT GAT GCT GGA AAC
 S   P   A   E   P   A   A   T   A   T   S   S   N   S   D   A   G   N 1413               1422               1431               1440               1449               1458
CCA GTG ACA ATG CAG GAA AGC CAT ACT GAA TCA GAA AGT GGT CTT GCT GAA TTA
 P   V   T   M   Q   E   S   H   T   E   S   E   S   G   L   A   E   L 1467               1476               1485               1494               1503               1512
GAC AGC TCT AAT GAA GAT GCA GGG ACA AAG ATG AGT GGT GAA AAA ATA TGA CTT
 D   S   S   N   E   D   A   G   T   K   M   S   G   E   K   I   *   L
```

FIGURE 1D

```
        1521       1530       1539       1548       1557       1566
TCC TTT TTG GTA ATA TTT TTG TGA TCT TTG ATG GTT TTT AAC CTA GGA AGT GTA 1575       1584       1593       1602       1611       1620
ATG TAT GCA TTT ATA TAA CTG TTT TGT TAT TTG AAT CTT GGA AAA CTA GTT TTA 1629       1638       1647       1656       1665       1674
TTA TAT TCA GAT AGC CTT GTT TTT TAA AAA GGC CTT TGC ATA CAC CTT TAT GAG 1683       1692       1701       1710       1719       1728
ATA GTG TAA AAT TGA CTA TTT ATA GTA CTA TGG ATT TAA TGA AAT TAT ATG TCA 1737       1746       1755       1764       1773       1782
TTT CAC ATT GTA TGC CAG AAA TTA GGC TAC CAA TTA TGA ATT AAA GTC AGT AGT 1791       1800       1809       1818       1827       1836
TAA ATT AAT ACT AGA TAG AAT TAG AAA TTT TGA TTA GAG AGA TTA TGC TAT ATT 1845       1854       1863       1872       1881       1890
ATG GAA AAA CTT GTT AAT GTA GAA TTA TAC TGC TTC ATA TTA TTT TAC CTA TTA
```

FIGURE 1E

```
     1899       1908       1917       1926       1935       1944
GTA CAC TCA TAG TTA GCT TTG TAA TAA ATT TAT GTT TTC TTT AAT AAT TTT AGT 1953       1962       1971       1980       1989       1998
TCT TCA AAG AAT GGC TGA TGC TGG CCT GTA ATT TTT CTT TCA AGG ATG ATA ATT 2007       2016       2025       2034       2043       2052
TGT GTG TTG TTT GAT TTG TTT ATA TTT TAC ATC TCT GTA GTT TTA TTT TTA GAA 2061       2070       2079       2088       2097       2106
GTT GTG AGA TAT TGG ATG TGT GGC TAT TTT TCC TTT CTC TGT ATT CTT TAT GAA 2115       2124       2133       2142       2151       2160
ACA TAA CTT TTG AAA AAC CTA TGT ATT ATT CAT ACA GCT TTG GTT TGT ATA TTC 2169       2178       2187       2196       2205       2214
TGT ATA GCC TAA CTA CAC ACA TCA AAA TGT ATG TCA ACC AAG TGT TTA GAA TGA 2223       2232       2241       2250       2259       2268
AAT TAT AAG TGT TTA AGT CCA AAT AAA GCA TGT GAT GTG GAA TAA TCA AAA AAA
```

```
241  ACDGIWDVMSNEELCEYVKSRLEVSDDLENVCNWVVDTCL   13177
241  ACDGIWDVMSNEELCEFVNSRLEVSDDLENVCNWVVDTCL   GI 247927
241  ACDGIWDVMSNEELCEFVKSRLEVSDDLENVCNWVVDTCL   GI 452526

281  HKGSRDNMSIVLVCFSNAPKVSDEAVKKDSELDKHLESRV   13177
281  HKGSRDNMSIVLVCFANAPKVSDEAVKRDLELDKHLESRV   GI 247927
281  HKGSRDNMSVVLVCFSNAPKVSEEAVKRDSELDKHLESRV   GI 452526

321  EEIMEKSGEEGMPDLAHVMRILSAENIPNLPPGGGLAGKR   13177
321  EEIMQKSGEEGMPDLAHVMRILSAENIPNLPPGGGLAGKR   GI 247927
321  EEIMQKSGEEGMPDLAHVMRILSAENIPNLPPGGGLAGKR   GI 452526

361  NVIEAVYSRLNPHRESDGASDEAEESGSQGKLVEALRQMR   13177
361  NVIEAVYSRLNPNKDNDGGAGD------------------   GI 247927
361  HVIEAVYSRLNPHKDNDGGAGD------------------   GI 452526

401  INHRGNYRQLLEEMLTSYRLAKVEGEESPAEPAATATSSN   13177
383  ---------LEDSLVA-----------------------   GI 247927
383  ---------LEDSLVA-----------------------   GI 452526

441  SDAGNPVTMQESHTESESGLAELDSSNEDAGTKMSGEKI   13177
390  -------------------------------------L   GI 247927
390  -------------------------------------L   GI 452526
```

FIGURE 2B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 478 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: THPIPLB01
        ( B ) CLONE: 13177

( x i ) SEQUENCE DESCRIPTION: SEQ ID NO:1:

```
Met Gly Ala Phe Leu Asp Lys Pro Lys Thr Glu Lys His Asn Ala His
 1               5                  10                  15
Gly Ala Gly Asn Gly Leu Arg Tyr Gly Leu Ser Ser Met Gln Gly Trp
             20              25              30
Arg Val Glu Met Glu Asp Ala His Thr Ala Val Val Gly Ile Pro His
         35              40              45
Gly Leu Glu Asp Trp Ser Phe Phe Ala Val Tyr Asp Gly His Ala Gly
     50              55              60
Ser Arg Val Ala Asn Tyr Cys Ser Thr His Leu Leu Glu His Ile Thr
65               70              75                          80
Thr Asn Glu Asp Phe Arg Ala Ala Gly Lys Gly Ser Ala Leu Glu
             85              90              95
Leu Ser Val Glu Asn Val Lys Asn Gly Ile Arg Thr Gly Phe Leu Lys
             100             105             110
Ile Asp Glu Tyr Met Arg Asn Phe Ser Asp Leu Arg Asn Gly Met Asp
         115             120             125
Arg Ser Gly Ser Thr Ala Val Gly Val Met Ile Ser Pro Lys His Ile
         130             135             140
Tyr Phe Ile Asn Cys Gly Asp Ser Arg Ala Val Leu Tyr Arg Asn Gly
145             150             155                         160
Gln Val Cys Phe Ser Thr Gln Asp His Lys Pro Cys Asn Pro Arg Glu
             165             170             175
Lys Glu Arg Ile Gln Asn Ala Gly Gly Ser Val Met Ile Gln Arg Val
             180             185             190
Asn Gly Ser Leu Ala Val Ser Arg Ala Leu Gly Asp Tyr Asp Tyr Lys
         195             200             205
Cys Val Asp Gly Lys Gly Pro Thr Glu Gln Leu Val Ser Pro Glu Pro
     210             215             220
Glu Val Tyr Glu Ile Leu Arg Ala Glu Glu Asp Glu Phe Ile Ile Leu
225             230             235                         240
Ala Cys Asp Gly Ile Trp Asp Val Met Ser Asn Glu Glu Leu Cys Glu
             245             250             255
Tyr Val Lys Ser Arg Leu Glu Val Ser Asp Asp Leu Glu Asn Val Cys
             260             265             270
Asn Trp Val Val Asp Thr Cys Leu His Lys Gly Ser Arg Asp Asn Met
         275             280             285
Ser Ile Val Leu Val Cys Phe Ser Asn Ala Pro Lys Val Ser Asp Glu
     290             295             300
Ala Val Lys Lys Asp Ser Glu Leu Asp Lys His Leu Glu Ser Arg Val
305             310             315                         320
Glu Glu Ile Met Glu Lys Ser Gly Glu Glu Gly Met Pro Asp Leu Ala
             325             330             335
His Val Met Arg Ile Leu Ser Ala Glu Asn Ile Pro Asn Leu Pro Pro
         340             345             350
Gly Gly Gly Leu Ala Gly Lys Arg Asn Val Ile Glu Ala Val Tyr Ser
         355             360             365
Arg Leu Asn Pro His Arg Glu Ser Asp Gly Ala Ser Asp Glu Ala Glu
         370             375             380
Glu Ser Gly Ser Gln Gly Lys Leu Val Glu Ala Leu Arg Gln Met Arg
385             390             395                         400
Ile Asn His Arg Gly Asn Tyr Arg Gln Leu Leu Glu Glu Met Leu Thr
             405             410             415
Ser Tyr Arg Leu Ala Lys Val Glu Gly Glu Glu Ser Pro Ala Glu Pro
             420             425             430
```

| Ala | Ala | Thr | Ala | Thr | Ser | Ser | Asn | Ser | Asp | Ala | Gly | Asn | Pro | Thr | Met |
|---|---|---|---|---|---|---|---|---|---|---|---|---|---|---|---|
| | | 435 | | | | | 440 | | | | | 445 | | | |

| Gln | Glu | Ser | His | Thr | Glu | Ser | Glu | Ser | Gly | Leu | Ala | Glu | Leu | Asp | Ser |
|---|---|---|---|---|---|---|---|---|---|---|---|---|---|---|---|
| | 450 | | | | | 455 | | | | | 460 | | | | |

| Ser | Asn | Glu | Asp | Ala | Gly | Thr | Lys | Met | Ser | Gly | Glu | Lys | Ile |
|---|---|---|---|---|---|---|---|---|---|---|---|---|---|
| 465 | | | | | 470 | | | | | 475 | | | |

( 2 ) INFORMATION FOR SEQ ID NO:2:

( i ) SEQUENCE CHARACTERISTICS:
        ( A ) LENGTH: 2268 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: 13177
        ( B ) CLONE: THPIPLB01

( x i ) SEQUENCE DESCRIPTION: SEQ ID NO:2:

```
ATATTGTACC TATCAGGCGT CAGCTCTCAA TCTAGATCCC TCCCTGGCCT CGGACTTATT      60
GCAAAACATG GGTGCTTTTT TGGATAAACC CAAAACTGAA AAACATAATG CTCATGGTGC     120
TGGGAATGGT TTACGTTATG GCCTGAGCAG CATGCAAGGA TGGAGAGTGG AAATGGAAGA     180
TGCACACACA GCTGTTGTAG GTATTCCTCA CGGCTTGGAA GACTGGTCAT TTTTTGCAGT     240
TTATGATGGT CATGCTGGAT CCCGAGTGGC AAATTACTGC TCAACACATT TATTAGAACA     300
CATCACTACT AACGAAGACT TTAGGGCAGC TGGAAAATCA GGATCTGCTC TTGAGCTTTC     360
AGTGGAAAAT GTTAAGAATG GTATCAGAAC TGGATTTTTG AAAATTGATG AATACATGCG     420
TAACTTTTCA GACCTCAGAA ACGGGATGGA CAGGAGTGGT TCAACTGCAG TGGGAGTTAT     480
GATTTCACCT AAGCATATCT ACTTTATCAA CTGTGGTGAT TCACGTGCTG TTCTGTATAG     540
GAATGGACAA GTCTGCTTTT CTACCCAGGA TCACAAACCT TGCAATCCAA GGGAAAAGGA     600
GCGAATCCAA AATGCAGGAG GCAGCGTGAT GATACAACGT GTTAATGGTT CATTAGCAGT     660
ATCTCGTGCT CTGGGGGACT ATGATTACAA GTGTGTTGAT GGCAAGGGCC AACAGAACA     720
ACTTGTTTCT CCAGAGCCTG AGGTTTATGA AATTTTAAGA GCAGAAGAGG ATGAATTTAT     780
CATCTTGGCT TGTGATGGGA TCTGGGATGT TATGAGTAAT GAGGAGCTCT GTGAATATGT     840
TAAATCTAGG CTTGAGGTAT CTGATGACCT GGAAAATGTG TGCAATTGGG TAGTGGACAC     900
TTGTTTACAC AAGGGAAGTC GAGATAACAT GAGTATTGTA CTAGTTTGCT TTCAAATGC     960
TCCCAAGGTC TCAGATGAAG CGGTGAAAAA AGATTCAGAG TTGGATAAGC ACTTGGAATC    1020
ACGGGTTGAA GAGATTATGG AGAAGTCTGG CGAGGAAGGA ATGCCTGATC TTGCCCATGT    1080
CATGCGCATC TTGTCTGCAG AAAATATCCC AAATTTGCCT CCTGGGGAG GTCTTGCTGG    1140
CAAGCGTAAT GTTATTGAAG CTGTTTATAG TAGACTGAAT CCACATAGAG AAAGTGATGG    1200
GGCCTCCGAT GAAGCAGAGG AAAGTGGATC ACAGGGAAAA TTGGTGGAAG CTCTCAGGCA    1260
AATGAGAATT AATCATAGGG GAAACTACCG ACAACTTCTG GAGGAGATGC TGACTAGTTA    1320
CAGGCTAGCT AAAGTAGAGG GAGAAGAAAG CCCTGCTGAA CCAGCTGCCA CAGCTACTTC    1380
TTCGAACAGT GATGCTGGAA ACCCAGTGAC AATGCAGGAA AGCCATACTG AATCAGAAAG    1440
TGGTCTTGCT GAATTAGACA GCTCTAATGA AGATGCAGGG ACAAAGATGA GTGGTGAAAA    1500
AATATGACTT TCCTTTTTGG TAATATTTTT GTGATCTTTG ATGGTTTTA ACCTAGGAAG    1560
TGTAATGTAT GCATTTATAT AACTGTTTTG TTATTTGAAT CTTGGAAAAC TAGTTTTATT    1620
ATATTCAGAT AGCCTTGTTT TTTAAAAAGG CCTTTGCATA CACCTTTATG AGATAGTGTA    1680
```

```
AAATTGACTA  TTTATAGTAC  TATGGATTTA  ATGAAATTAT  ATGTCATTTC  ACATTGTATG   1740

CCAGAAATTA  GGCTACCAAT  TATGAATTAA  AGTCAGTAGT  TAAATTAATA  CTAGATAGAA   1800

TTAGAAATTT  TGATTAGAGA  GATTATGCTA  TATTATGGAA  AAACTTGTTA  ATGTAGAATT   1860

ATACTGCTTC  ATATTATTTT  ACCTATTAGT  ACACTCATAG  TTAGCTTTGT  AATAAATTTA   1920

TGTTTTCTTT  AATAATTTTA  GTTCTTCAAA  GAATGGCTGA  TGCTGGCCTG  TAATTTTTCT   1980

TTCAAGGATG  ATAATTTGTG  TGTTGTTTGA  TTTGTTTATA  TTTTACATCT  CTGTAGTTTT   2040

ATTTTTAGAA  GTTGTGAGAT  ATTGGATGTG  TGGCTATTTT  TCCTTTCTCT  GTATTCTTTA   2100

TGAAACATAA  CTTTTGAAAA  ACCTATGTAT  TATTCATACA  GCTTTGGTTT  GTATATTCTG   2160

TATAGCCTAA  CTACACACAT  CAAAATGTAT  GTCAACCAAG  TGTTTAGAAT  GAAATTATAA   2220

GTGTTTAAGT  CCAAATAAAG  CATGTGATGT  GGAATAATCA  AAAAAAA                  2268
```

( 2 ) INFORMATION FOR SEQ ID NO:3:

( i ) SEQUENCE CHARACTERISTICS:
        ( A ) LENGTH: 390 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1247927

( x i ) SEQUENCE DESCRIPTION: SEQ ID NO:3:

```
Met  Gly  Ala  Phe  Leu  Asp  Lys  Pro  Lys  Thr  Glu  Lys  His  Asn  Ala  His
 1                  5                   10                  15

Gly  Ala  Gly  Asn  Gly  Leu  Arg  Tyr  Gly  Leu  Ser  Ser  Met  Gln  Gly  Trp
               20                  25                  30

Arg  Val  Glu  Met  Glu  Asp  Ala  His  Thr  Ala  Val  Val  Gly  Ile  Pro  His
          35                  40                  45

Gly  Leu  Glu  Asp  Trp  Ser  Phe  Phe  Ala  Val  Tyr  Asp  Gly  His  Ala  Gly
          50                  55                  60

Ser  Arg  Val  Ala  Asn  Tyr  Cys  Ser  Thr  His  Leu  Glu  His  Ile  Thr
65                       70                  75                       80

Thr  Asn  Glu  Asp  Phe  Arg  Ala  Ala  Asp  Lys  Ser  Gly  Phe  Ala  Leu  Glu
                    85                  90                       95

Pro  Ser  Val  Glu  Asn  Val  Lys  Thr  Gly  Ile  Arg  Thr  Gly  Phe  Leu  Lys
               100                 105                 110

Ile  Asp  Glu  Tyr  Met  Arg  Asn  Phe  Ser  Asp  Leu  Arg  Asn  Gly  Met  Asp
          115                 120                 125

Arg  Ser  Gly  Ser  Thr  Ala  Val  Gly  Val  Met  Ile  Ser  Pro  Thr  His  Ile
          130                 135                 140

Tyr  Phe  Ile  Asn  Cys  Gly  Asp  Ser  Arg  Ala  Val  Leu  Cys  Arg  Asn  Gly
145                      150                 155                      160

Gln  Val  Cys  Phe  Ser  Thr  Gln  Asp  His  Lys  Pro  Cys  Asn  Pro  Met  Glu
                    165                 170                 175

Lys  Glu  Arg  Ile  Gln  Asn  Ala  Gly  Gly  Ser  Val  Met  Ile  Gln  Arg  Val
               180                 185                 190

Asn  Gly  Ser  Leu  Ala  Val  Ser  Arg  Ala  Leu  Gly  Asp  Tyr  Asp  Tyr  Lys
               195                 200                 205

Cys  Val  Asp  Gly  Lys  Gly  Pro  Thr  Glu  Gln  Leu  Val  Ser  Pro  Glu  Pro
          210                 215                 220

Glu  Val  Tyr  Glu  Ile  Leu  Arg  Ala  Glu  Glu  Asp  Glu  Phe  Val  Val  Leu
225                      230                 235                      240
```

| Ala | Cys | Asp | Gly | Ile | Trp | Asp | Val | Met | Ser | Asn | Glu | Glu | Leu | Cys | Glu |
|---|---|---|---|---|---|---|---|---|---|---|---|---|---|---|---|
| | | | | 245 | | | | 250 | | | | | | 255 | |

| Phe | Val | Asn | Ser | Arg | Leu | Glu | Val | Ser | Asp | Asp | Leu | Glu | Asn | Val | Cys |
|---|---|---|---|---|---|---|---|---|---|---|---|---|---|---|---|
| | | | 260 | | | | | 265 | | | | | 270 | | |

| Asn | Trp | Val | Val | Asp | Thr | Cys | Leu | His | Lys | Gly | Ser | Arg | Asp | Asn | Met |
|---|---|---|---|---|---|---|---|---|---|---|---|---|---|---|---|
| | | 275 | | | | | 280 | | | | | 285 | | | |

| Ser | Ile | Val | Leu | Val | Cys | Phe | Ala | Asn | Ala | Pro | Lys | Val | Ser | Asp | Glu |
|---|---|---|---|---|---|---|---|---|---|---|---|---|---|---|---|
| | 290 | | | | | 295 | | | | | 300 | | | | |

| Ala | Val | Lys | Arg | Asp | Leu | Glu | Leu | Asp | Lys | His | Leu | Glu | Ser | Arg | Val |
|---|---|---|---|---|---|---|---|---|---|---|---|---|---|---|---|
| 305 | | | | | 310 | | | | | 315 | | | | | 320 |

| Glu | Glu | Ile | Met | Gln | Lys | Ser | Gly | Glu | Glu | Gly | Met | Pro | Asp | Leu | Ala |
|---|---|---|---|---|---|---|---|---|---|---|---|---|---|---|---|
| | | | | 325 | | | | | 330 | | | | | 335 | |

| His | Val | Met | Arg | Ile | Leu | Ser | Ala | Glu | Asn | Ile | Pro | Asn | Leu | Pro | Pro |
|---|---|---|---|---|---|---|---|---|---|---|---|---|---|---|---|
| | | | 340 | | | | | 345 | | | | | 350 | | |

| Gly | Gly | Gly | Leu | Ala | Gly | Lys | Arg | Asn | Val | Ile | Glu | Ala | Val | Tyr | Ser |
|---|---|---|---|---|---|---|---|---|---|---|---|---|---|---|---|
| | | 355 | | | | | 360 | | | | | 365 | | | |

| Arg | Leu | Asn | Pro | Asn | Lys | Asp | Asn | Asp | Gly | Gly | Ala | Gly | Asp | Leu | Glu |
|---|---|---|---|---|---|---|---|---|---|---|---|---|---|---|---|
| | 370 | | | | | 375 | | | | | 380 | | | | |

| Asp | Ser | Leu | Val | Ala | Leu |
|---|---|---|---|---|---|
| 385 | | | | | 390 |

(2) INFORMATION FOR SEQ ID NO:4:

(i) SEQUENCE CHARACTERISTICS:
        (A) LENGTH: 478 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1452526

(xi) SEQUENCE DESCRIPTION: SEQ ID NO:4:

| Met | Gly | Ala | Phe | Leu | Asp | Lys | Pro | Lys | Thr | Glu | Lys | His | Asn | Ala | His |
|---|---|---|---|---|---|---|---|---|---|---|---|---|---|---|---|
| 1 | | | | 5 | | | | | 10 | | | | | 15 | |

| Gly | Ala | Gly | Asn | Gly | Leu | Arg | Tyr | Gly | Leu | Ser | Ser | Met | Gln | Gly | Trp |
|---|---|---|---|---|---|---|---|---|---|---|---|---|---|---|---|
| | | | 20 | | | | | 25 | | | | | 30 | | |

| Arg | Val | Glu | Met | Glu | Asp | Ala | His | Thr | Ala | Val | Val | Gly | Ile | Pro | His |
|---|---|---|---|---|---|---|---|---|---|---|---|---|---|---|---|
| | | | 35 | | | | | 40 | | | | | 45 | | |

| Gly | Leu | Glu | Asp | Trp | Ser | Phe | Phe | Ala | Val | Tyr | Asp | Gly | His | Ala | Gly |
|---|---|---|---|---|---|---|---|---|---|---|---|---|---|---|---|
| | 50 | | | | | 55 | | | | | 60 | | | | |

| Ser | Arg | Val | Ala | Asn | Tyr | Cys | Ser | Thr | His | Leu | Leu | Glu | His | Ile | Thr |
|---|---|---|---|---|---|---|---|---|---|---|---|---|---|---|---|
| 65 | | | | | 70 | | | | | 75 | | | | | 80 |

| Thr | Asn | Glu | Asp | Phe | Arg | Ala | Ala | Gly | Lys | Ser | Gly | Ser | Ala | Leu | Glu |
|---|---|---|---|---|---|---|---|---|---|---|---|---|---|---|---|
| | | | | 85 | | | | | 90 | | | | | 95 | |

| Leu | Ser | Val | Glu | Asn | Val | Lys | Asn | Gly | Ile | Arg | Thr | Gly | Phe | Leu | Lys |
|---|---|---|---|---|---|---|---|---|---|---|---|---|---|---|---|
| | | | 100 | | | | | 105 | | | | | 110 | | |

| Ile | Asp | Glu | Tyr | Met | Arg | Asn | Phe | Ser | Asp | Leu | Arg | Asn | Gly | Met | Asp |
|---|---|---|---|---|---|---|---|---|---|---|---|---|---|---|---|
| | | 115 | | | | | 120 | | | | | 125 | | | |

| Arg | Ser | Gly | Ser | Thr | Ala | Val | Gly | Val | Met | Ile | Ser | Pro | Lys | His | Ile |
|---|---|---|---|---|---|---|---|---|---|---|---|---|---|---|---|
| | 130 | | | | | 135 | | | | | 140 | | | | |

| Tyr | Phe | Ile | Asn | Cys | Gly | Asp | Ser | Arg | Ala | Val | Leu | Tyr | Arg | Asn | Gly |
|---|---|---|---|---|---|---|---|---|---|---|---|---|---|---|---|
| 145 | | | | | 150 | | | | | 155 | | | | | 160 |

| Gln | Val | Cys | Phe | Ser | Thr | Gln | Asp | His | Lys | Pro | Cys | Asn | Pro | Arg | Glu |
|---|---|---|---|---|---|---|---|---|---|---|---|---|---|---|---|
| | | | | 165 | | | | | 170 | | | | | 175 | |

-continued

| Lys | Glu | Arg | Ile 180 | Gln | Asn | Ala | Gly | Gly 185 | Ser | Val | Met | Ile | Gln 190 | Arg | Val |
| Asn | Gly | Ser 195 | Leu | Ala | Val | Ser | Arg 200 | Ala | Leu | Gly | Asp | Tyr 205 | Asp | Tyr | Lys |
| Cys | Val 210 | Asp | Gly | Lys | Gly | Pro 215 | Thr | Glu | Gln | Leu | Val 220 | Ser | Pro | Glu | Pro |
| Glu 225 | Val | Tyr | Glu | Ile | Leu 230 | Arg | Ala | Glu | Glu | Asp 235 | Glu | Phe | Ile | Ile | Leu 240 |
| Ala | Cys | Asp | Gly | Ile 245 | Trp | Asp | Val | Met | Ser 250 | Asn | Glu | Glu | Leu | Cys 255 | Glu |
| Tyr | Val | Lys | Ser 260 | Arg | Leu | Glu | Val | Ser 265 | Asp | Asp | Leu | Glu | Asn 270 | Val | Cys |
| Asn | Trp | Val 275 | Val | Asp | Thr | Cys | Leu 280 | His | Lys | Gly | Ser | Arg 285 | Asp | Asn | Met |
| Ser | Ile 290 | Val | Leu | Val | Cys | Phe 295 | Ser | Asn | Ala | Pro | Lys 300 | Val | Ser | Asp | Glu |
| Ala 305 | Val | Lys | Lys | Asp | Ser 310 | Glu | Leu | Asp | Lys | His 315 | Leu | Glu | Ser | Arg | Val 320 |
| Glu | Glu | Ile | Met | Glu 325 | Lys | Ser | Gly | Glu | Glu 330 | Gly | Met | Pro | Asp | Leu 335 | Ala |
| His | Val | Met | Arg 340 | Ile | Leu | Ser | Ala | Glu 345 | Asn | Ile | Pro | Asn | Leu 350 | Pro | Pro |
| Gly | Gly | Gly 355 | Leu | Ala | Gly | Lys | Arg 360 | Asn | Val | Ile | Glu | Ala 365 | Val | Tyr | Ser |
| Arg | Leu 370 | Asn | Pro | His | Arg | Glu 375 | Ser | Asp | Gly | Ala | Ser 380 | Asp | Glu | Ala | Glu |
| Glu 385 | Ser | Gly | Ser | Gln | Gly 390 | Lys | Leu | Val | Glu | Ala 395 | Leu | Arg | Gln | Met | Arg 400 |
| Ile | Asn | His | Arg | Gly 405 | Asn | Tyr | Arg | Gln | Leu 410 | Leu | Glu | Glu | Met | Leu 415 | Thr |
| Ser | Tyr | Arg | Leu 420 | Ala | Lys | Val | Glu | Gly 425 | Glu | Glu | Ser | Pro | Ala 430 | Glu | Pro |
| Ala | Ala | Thr 435 | Ala | Thr | Ser | Ser | Asn 440 | Ser | Asp | Ala | Gly | Asn 445 | Pro | Thr | Met |
| Gln | Glu 450 | Ser | His | Thr | Glu | Ser 455 | Glu | Ser | Gly | Leu | Ala 460 | Glu | Leu | Asp | Ser |
| Ser 465 | Asn | Glu | Asp | Ala | Gly 470 | Thr | Lys | Met | Ser | Gly 475 | Glu | Lys | Ile | | |

HUMAN PROTEIN PHOSPHATASE

FIELD OF THE INVENTION

This invention relates to nucleic acid and amino acid sequences of a human protein phosphatase and to the use of these sequences in the diagnosis, prevention, and treatment of inflammation and disorders associated with cell proliferation and apoptosis.

BACKGROUND OF THE INVENTION

The protein phosphorylation/dephosphorylation cycle is one of the major regulatory mechanisms employed by eukaryotic cells to control cellular activities. It is estimated that more than 10% of the active proteins in a typical mammalian cell are phosphorylated. During protein phosphorylation/dephosphorylation, phosphate groups are transferred from adenosine triphosphate molecules to a protein by protein kinases and are removed from the protein by protein phosphatases.

Protein phosphatases function in cellular signaling events that regulate cell growth and differentiation, cell-to-cell contacts, the cell cycle, and oncogenesis. Three protein phosphatase families have been identified as evolutionarily-distinct. These include the serine/threonine phosphatases, the protein tyrosine phosphatases, and the acid/alkaline phosphatases (Carbonneau H. and Tonks N. K. (1992) Annu. Rev. Cell Biol. 8:463–93).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP-I, PP-IIA, PP-IIB, and PP-IIC.

PP-I dephosphorylates many of the proteins phosphorylated by cylic AMP-dependent protein kinase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine kinases. PP-IIB, or calcineurin (Cn), is a $Ca^{+2}$-activated phosphatase; it is involved in the regulation of such diverse cellular functions as ion channel regulation, neuronal transmission, gene transcription, muscle glycogen metabolism, and lymphocyte activation.

PP-IIC is a $Mg^{++}$-dependent phosphatase which participates in a wide variety of functions including regulating cyclic AMP-activated protein-kinase activity, $Ca^{++}$-dependent signal transduction, tRNA splicing, and signal transmission related to heat shock responses. PP-IIC is a monomeric protein with a molecular mass of about 40–45 kDa. One α and several β isoforms of PP-IIC have been identified (Wenk, J. et al. (1992) FEBS Lett. 297: 135–138; Terasawa, T. et al. (1993) Arch. Biochem. Biophys. 307: 342–349; and Kato, S. et al. (1995) Arch. Biochem. Biophys. 318: 387–393).

The discovery of a new human protein phosphatase and the polynucleotides encoding it satisfies a need in the art by providing new compositions which are useful in the diagnosis, prevention and treatment of inflammation and disorders associated with cell proliferation and apoptosis.

SUMMARY OF THE INVENTION

The invention features a substantially purified polypeptide, human protein phosphatase (PROPHO), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding PROPHO under conditions suitable for the expression of the polypeptide; and b) recovering the polypeptide from the host cell culture.

The invention also provides a pharmaceutical composition comprising a substantially purified PROPHO having the amino acid sequence of SEQ ID NO:1 in conjunction with a suitable pharmaceutical carrier.

The invention also provides a purified antagonist which decreases the effect of the polypeptide of SEQ ID NO:1. In one aspect, the invention provides a purified antibody which binds to a polypeptide comprising at least a fragment of the amino acid sequence of SEQ ID NO:1.

Still further, the invention provides a purified agonist which modulates the activity of the polypeptide of SEQ ID NO:1.

The invention also provides a method for stimulating cell proliferation comprising administering to a cell an effective amount of purified PROPHO.

The invention also provides a method for treating a disorder associated with increased apoptosis comprising administering to a subject in need of such treatment an effective amount of the pharmaceutical composition comprising purified PROPHO.

The invention also provides a method for treating a disorder associated with cancer comprising administering to a subject in need of such treatment an effective amount of an antagonist which decreases the effect of PROPHO.

The invention also provides a method for treating inflammation comprising administering to a subject in need of such treatment an effective amount of an antagonist which decreases the effect of PROPHO.

The invention also provides a method for detecting a polynucleotide which encodes PROPHO in a biological sample comprising the steps of: a) hybridizing a polynucleotide sequence complementary to PROPHO (SEQ ID NO:1) to nucleic acid material of a biological sample, thereby forming a hybridization complex; and b) detecting the hybridization complex, wherein the presence of the complex correlates with the presence of a polynucleotide encoding PROPHO in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of PROPHO. The alignment was produced using MACDNASIS PRO software (Hitachi Software Engineering Co. Ltd. San Bruno, Calif.).

FIGS. 2A and 2B show the amino acid sequence alignments among PROPHO (SEQ ID NO:1), a rat protein phosphatase IIC isoform, PP2C2 (GI 247927; SEQ ID NO:3), and a mouse protein phosphatase IIC β isoform, MPPβ1 (GI 452526; SEQ ID NO:4), produced using the multisequence alignment program of DNASTAR™ software (DNASTAR Inc, Madison Wis.).

DESCRIPTION OF THE INVENTION

Figure 3A:
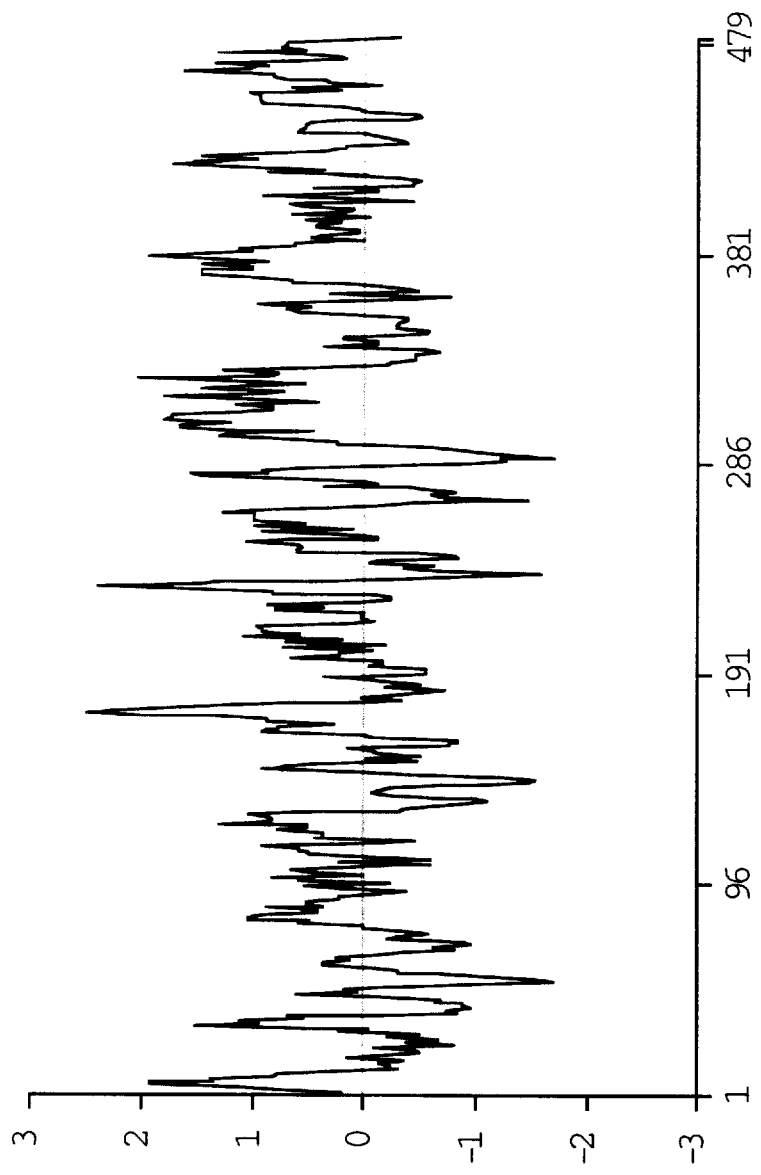
FIGS. 3A and 3B show the hydrophobicity plots for PROPHO, SEQ ID NO:1 and PP2C2 (SEQ ID NO:3), respectively. The positive X axis reflects amino acid position, and the negative Y axis, hydrophobicity (MACDNASIS PRO).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

PROPHO, as used herein, refers to the amino acid sequences of substantially purified PROPHO obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to PROPHO, increases or prolongs the duration of the effect of PROPHO. Agonists may include proteins, nucleic acids, carbohydrates, or any other molecules which bind to and modulate the effect of PROPHO.

An "allele" or "allelic sequence", as used herein, is an alternative form of the gene encoding PROPHO. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding PROPHO as used herein include those with deletions, insertions, or substitutions of different nucleotides resulting in a polynucleotide that encodes the same or a functionally equivalent PROPHO. Included within this definition are polymorphisms which may or may not be readily detectable using a particular oligonucleotide probe of the polynucleotide encoding PROPHO, and improper or unexpected hybridization to alleles, with a locus other than the normal chromosomal locus for the polynucleotide sequence encoding PROPHO. The encoded protein may also be "altered" and contain deletions, insertions, or substitutions of amino acid residues which produce a silent change and result in a functionally equivalent PROPHO. Deliberate amino acid substitutions may be made on the basis of similarity in polarity, charge, solubility, hydrophobicity, hydrophilicity, and/or the amphipathic nature of the residues as long as the biological or immunological activity of PROPHO is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of PROPHO are preferably about 5 to about 15 amino acids in length and retain the biological activity or the immunological activity of PROPHO. Where "amino acid sequence" is recited herein to refer to an amino acid sequence of a naturally occurring protein molecule, amino acid sequence, and like terms, are not meant to limit the "amino acid sequence" to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to PROPHO, decreases the amount or the duration of the effect of the biological or immunological activity of PROPHO. Antagonists may include proteins, nucleic acids, carbohydrates, or any other molecules which and decrease the effect of PROPHO.

As used herein, the term "antibody" refers to intact molecules as well as fragments thereof, such as Fab, F(ab')$_2$, and Fv, which are capable of binding the epitopic determinant. Antibodies that bind PROPHO polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic PROPHO, or any oligopeptide thereof, to induce a specific immune response in appropriate animals or cells and to bind with specific antibodies.

The terms "complementary" or "complementarity", as used herein, refer to the natural binding of polynucleotides by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding PROPHO (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding PROPHO in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to PROPHO or the encoded PROPHO. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 1M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to a high-density array of distinct polynucleotides or oligonucleotides synthesized on a substrate, such as paper, nylon or other type of membrane, filter, chip, glass slide, or any other suitable solid support.

The term "modulate", as used herein, refers to a change in the activity of PROPHO. For example, modulation may cause an increase or a decrease in protein activity, binding characteristics, or any other biological, functional or immunological properties of PROPHO.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides, preferably at least 100 nucleotides, more preferably at least 1000 nucleotides, and most preferably at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "compris- ing at least a portion of the amino acid sequence of SEQ ID NO:1" encompasses the full-length PROPHO and fragments thereof.

The term "sample", as used herein, is used in its broadest sense. A biological sample suspected of containing nucleic acid encoding PROPHO, or fragments thereof, or PROPHO itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody, and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of PROPHO, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human protein phosphatase (hereinafter referred to as "PROPHO"), the polynucleotides encoding PROPHO, and the use of these compositions for the diagnosis, prevention, or treatment of inflammation and disorders associated with cell proliferation and apoptosis.

Nucleic acids encoding the PROPHO of the present invention were first identified in Incyte Clone 13177 from a prostate tumor tissue cDNA library (THP1PLB01) using a computer search for amino acid sequence alignments. A consensus sequence, SEQ ID NO:2, was derived from the following overlapping and/or extended nucleic acid sequences: Incyte Clones 1579311 (DUODNOT01), 2503647 (CONUTUT01), 91657 (HYPONOB01), 723108 (SYNOOAT01), and 13177 (THP1PLB01).

Figure 2A:
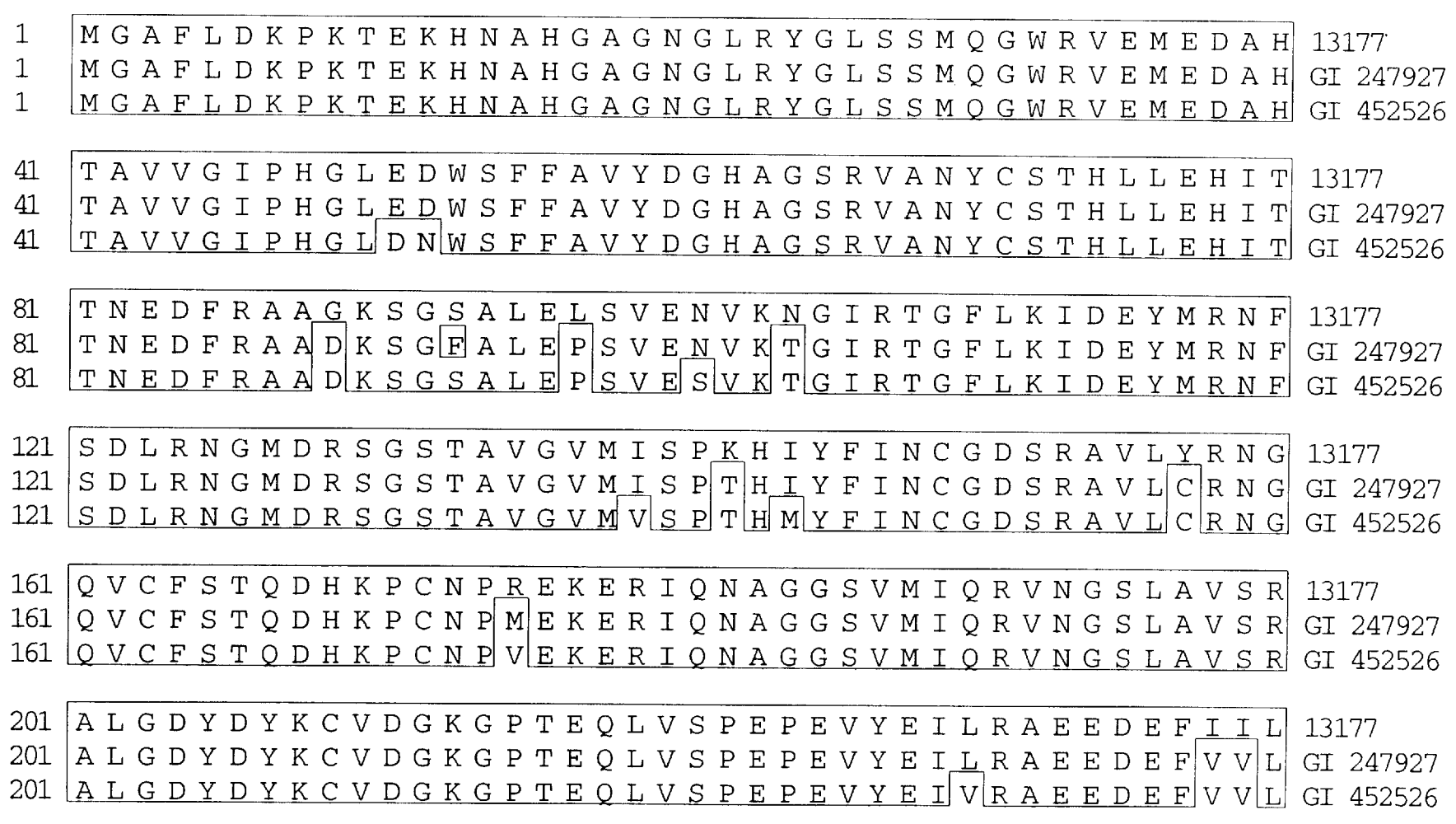
Figure 3B:
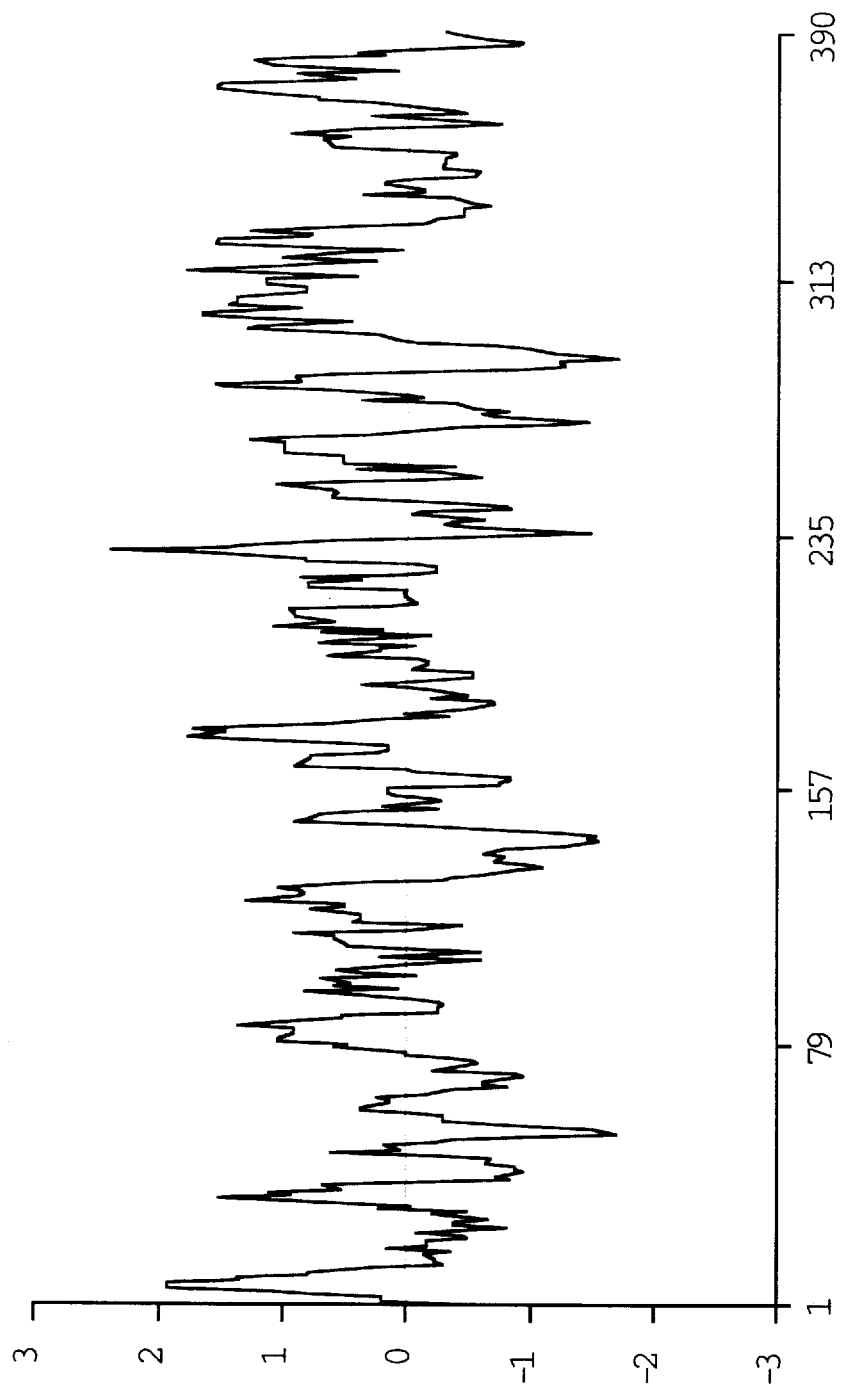

In one embodiment, the invention encompasses a polypeptide comprising the amino acid sequence of SEQ ID NO:1, as shown in FIGS. 1A through 1G. PROPHO is 222 amino acids in length and has a protein phosphatase 2C signature encompassing residues F55–A63. PROPHO has three potential N-glycosylation sites at N119, N193 and N287; one potential cAMP- and cGMP-dependent protein kinase phosphorylation site encompassing residues K307–S310; sixteen potential casein kinase II phosphorylation sites encompassing residues T80–E83, T81–D84, S93–E96, S165–D168, S250–E253, S260–E263, S310–D313, S318–E321, S327–E330, S428–E431, S439–D442, T447–E450, S451–E454, T453–E456, S464–E467, and S465–D468; two potential tyrosine kinase phosphorylation sites encompassing residues R200–Y207 and R360–Y367; and three potential protein kinase C phosphorylation sites encompassing residues T10–K12, S140–K142, and S417–R419. As shown in FIGS. 2A and 2B, PROPHO has chemical and structural homology with a rat protein phosphatase IIC isoform, PP2C2 (GI 247927; SEQ ID NO:3) and a mouse protein phosphatase IIC β isoform, MPPβ1 (GI 452526; SEQ ID NO:4). In particular, PROPHO shares 99% and 98% identity with PP2C2 and MPPβ1, respectively. As illustrated by FIGS. 3A and 3B, PROPHO and PP2C2 have rather similar hydrophobicity plots. Northern analysis shows the expression of this sequence in various libraries, at least 48% of which are immortalized or cancerous, at least 16% of which involve immune response, and at least 20% of which involve infant/fetal tissues or organs.

The invention also encompasses PROPHO variants. A preferred PROPHO variant is one having at least 80%, and more preferably 90%, amino acid sequence identity to the PROPHO amino acid sequence (SEQ ID NO:1) and which retain the biological, immunological or other functional characteristics of the activity of CARIN. A most preferred PROPHO variant is one having at least 95% amino acid sequence identity to SEQ ID NO:1.

The invention also encompasses polynucleotides which encode PROPHO. Accordingly, any nucleic acid sequence which encodes the amino acid sequence of PROPHO can be used to produce recombinant molecules which express PROPHO. In a particular embodiment, the invention encompasses the polynucleotide comprising the nucleic acid sequence of SEQ ID NO:2 as shown in FIGS. 1A through 1G.

It will be appreciated by those skilled in the art that as a result of the degeneracy of the genetic code, a multitude of nucleotide sequences encoding PROPHO, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring PROPHO, and all such variations are to be considered as being specifically disclosed.

Although nucleotide sequences which encode PROPHO and its variants are preferably capable of hybridizing to the nucleotide sequence of the naturally occurring PROPHO under appropriately selected conditions of stringency, it may be advantageous to produce nucleotide sequences encoding PROPHO or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PROPHO and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode PROPHO and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding PROPHO or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase polymerase (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (Gibco/BRL Gaithersburg, Md.). Preferably, the process is automated with machines such as the Hamilton MICRO LAB 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding PROPHO may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PROPHO may be used in recombinant DNA molecules to direct expression of PROPHO, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PROPHO.

As will be understood by those of skill in the art, it may be advantageous to produce PROPHO-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PROPHO encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PROPHO may be ligated to a heterologous sequence to encode a fusion protein. For example, to screen peptide libraries for inhibitors of PROPHO activity, it may be useful to encode a chimeric PROPHO protein that can be recognized by a commercially available antibody. A fusion protein may also be engineered to contain a cleavage site located between the PROPHO encoding sequence and the heterologous protein sequence, so that PROPHO may be cleaved and purified away from the heterologous moiety.

In another embodiment, sequences encoding PROPHO may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of PROPHO, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) Proteins, Structures and Molecular Principles, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of PROPHO, or any part thereof, may be altered during direct synthesis and/or combined using chemical methods with sequences from other proteins, or any part thereof, to produce a variant polypeptide.

In order to express a biologically active PROPHO, the nucleotide sequences encoding PROPHO or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PROPHO and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding PRO-PHO. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PROPHO, vectors based on SV40 or EBV may be used with an appropriate selectable marker.

In bacterial systems, a number of expression vectors may be selected depending upon the use intended for PROPHO. For example, when large quantities of PROPHO are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding PROPHO may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding PROPHO may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express PROPHO. For example, in one such system, *Autographa californica* nuclear polyhedrosis virus (AcNPV) is used as a vector to express foreign genes in *Spodoptera frugiperda* cells or in Trichoplusia larvae. The sequences encoding PROPHO may be cloned into a non-essential region of the virus, such as the polyhedrin gene, and placed under control of the polyhedrin promoter. Successful insertion of PROPHO will render the polyhedrin gene inactive and produce recombinant virus lacking coat protein. The recombinant viruses may then be used to infect, for example, *S. frugiperda* cells or Trichoplusia larvae in which PROPHO may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding PROPHO may be ligated into an adenovirus transcription/translation complex consisting of the late promoter and tripartite leader sequence. Insertion in a non-essential E1 or E3 region of the viral genome may be used to obtain a viable virus which is capable of expressing PROPHO in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding PROPHO. Such signals include the ATG initiation codon and adjacent sequences. In cases where sequences encoding PROPHO, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express PROPHO may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding PROPHO is inserted within a marker gene sequence, transformed cells containing sequences encoding PROPHO can be identified by the absence of marker gene function. Alternatively, a marker gene can be placed in tandem with a sequence encoding PROPHO under the control of a single promoter. Expression of the marker gene in response to induction or selection usually indicates expression of the tandem gene as well.

Alternatively, host cells which contain the nucleic acid sequence encoding PROPHO and express PROPHO may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding PROPHO can be detected by DNA-DNA or DNA-RNA hybridization or amplification using probes or fragments or fragments of polynucleotides encoding PROPHO. Nucleic acid amplification based assays involve the use of oligonucleotides or oligomers based on the sequences encoding PROPHO to detect transformants containing DNA or RNA encoding PROPHO.

A variety of protocols for detecting and measuring the expression of PROPHO, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PROPHO is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PROPHO include oligolabeling, nick translation, end-labeling or PCR amplification using a labeled nucleotide. Alternatively, the sequences encoding PROPHO, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6, and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding PROPHO may be cultured under conditions suitable for the expression and recovery of the protein from cell culture. The protein produced by a transformed cell may be secreted or contained intracellularly depending on the sequence and/ or the vector used. As will be understood by those of skill in the art, expression vectors containing polynucleotides which encode PROPHO may be designed to contain signal sequences which direct secretion of PROPHO through a prokaryotic or eukaryotic cell membrane. Other constructions may be used to join sequences encoding PROPHO to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and PROPHO may be used to facilitate purification. One such expression vector provides for expression of a fusion protein containing PROPHO and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying PROPHO from the fusion protein. A discussion of vectors which contain fusion proteins is provided in Kroll, D. J. et al. (1993; DNA Cell Biol. 12:441–453).

In addition to recombinant production, fragments of PROPHO may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of PROPHO may be chemically synthesized separately and combined using chemical methods to produce the full length molecule.

THERAPEUTICS

Chemical and structural homology exists among PROPHO, a PP2C2 (GI 247927; SEQ ID NO:3), and a mouse protein phosphatase IIC β isoform, MPPβ1 (GI 452526; SEQ ID NO:4). Northern analysis shows that the expression of PROPHO is associated with cancer, inflammation and immune response, and fetal/infant development.

During fetal development, decreased expression of PROPHO may cause an increase in apoptosis with no adverse effects to the subject. However, in other situations and in adults, decreased expression of PROPHO may cause an increase in apoptosis which is detrimental to the subject. Therefore, in one embodiment, PROPHO or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, an agonist which is specific for PROPHO may be used to prevent or treat a disorder associated with increased apoptosis including, but not limited to, those listed above.

In still another embodiment, a vector capable of expressing PROPHO, or a fragment or a derivative thereof, may be used to prevent or treat a disorder associated with increased apoptosis including, but not limited to, those listed above.

In a further embodiment, PROPHO or a fragment or derivative thereof may be added to cells to stimulate cell proliferation. In particular, PROPHO may be added to a cell or cells in vivo using delivery mechanisms such as liposomes, viral based vectors, or electroinjection for the purpose of promoting regeneration or cell differentiation of the cell or cells. In addition, PROPHO may be added to a cell, cell line, tissue, or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for PROPHO may be administered to a cell to stimulate cell proliferation, as described above.

In another further embodiment, a vector capable of expressing PROPHO, or a fragment or a derivative thereof, may be administered to a cell or cells in vivo using delivery mechanisms, or to a cell to stimulate cell proliferation, as described above.

Increased expression of PROPHO appears to be associated with increased cell proliferation. Therefore, in one embodiment, an antagonist of PROPHO, or a fragment or a derivative thereof, may be administered to a subject to prevent or treat cancer. Such disorders include various types of cancer including, but not limited to, adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for PROPHO may be used directly as an antagonist, or indirectly as a targeting or delivery mechanism for bringing a pharmaceutical agent to cells or tissue which express PROPHO.

In still another embodiment, a vector expressing the complementary sequence or antisense of the polynucleotide encoding PROPHO, or a fragment or a derivative thereof, may be administered to a subject to prevent or treat a disorder associated with cell proliferation including, but not limited to, the types of cancer listed above.

In a further embodiment, an antagonist of PROPHO or a fragment or a derivative thereof, may be administered to a subject to prevent or treat inflammation of any type and, in particular, that which results from a particular disorder or conditions. Such disorders and conditions associated with inflammation include, but are not limited to, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation,osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for PROPHO may be used directly as an antagonist, or indirectly as a targeting or delivery mechanism for bringing a pharmaceutical agent to cells or tissue which express PROPHO.

In another further embodiment, a vector expressing the complementary sequence or antisense of the polynucleotide encoding PROPHO, or a fragment or a derivative thereof, may be administered to a subject to prevent or treat inflammation of any type including, but not limited to, those listed above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of PROPHO may be produced using methods which are generally known in the art. In particular, purified PROPHO may be used to produce antibodies or to screen libraries of pharmaceutical agents to identify those which specifically bind PROPHO.

Antibodies to PROPHO may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PROPHO or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PROPHO have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of PROPHO amino acids may be fused with those of another protein such as keyhole limpet hemocyanin and antibody produced against the chimeric molecule.

Monoclonal antibodies to PROPHO may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce PROPHO-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for PROPHO may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PROPHO and its specific antibody. A two-site, monoclonal-based immunoassay utilizing monoclonal antibodies reactive to two non-interfering PROPHO epitopes is preferred, but a competitive binding assay may also be employed (Maddox, supra).

In another embodiment of the invention, the polynucleotides encoding PROPHO, or any fragment or complement thereof, may be used for therapeutic purposes. In one aspect, the complement of the polynucleotide encoding PROPHO may be used in situations in which it would be desirable to block the transcription of the mRNA. In particular, cells may be transformed with sequences complementary to polynucleotides encoding PROPHO. Thus, complementary molecules or fragments may be used to modulate PROPHO activity, or to achieve regulation of gene function. Such technology is now well known in the art, and sense or antisense oligonucleotides or larger fragments, can be designed from various locations along the coding or control regions of sequences encoding PROPHO.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding PROPHO. These techniques are described both in Sambrook et al. (supra) and in Ausubel et al. (supra).

Genes encoding PROPHO can be turned off by transforming a cell or tissue with expression vectors which express high levels of a polynucleotide or fragment thereof which encodes PROPHO. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding PROPHO (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PROPHO.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PROPHO. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PROPHO, antibodies to PROPHO, mimetics, agonists, antagonists, or inhibitors of PROPHO. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PROPHO, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PROPHO or fragments thereof, antibodies of PROPHO, agonists, antagonists or inhibitors of PROPHO, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind PROPHO may be used for the diagnosis of conditions or diseases characterized by expression of PROPHO, or in assays to monitor patients being treated with PROPHO, agonists, antagonists or inhibitors. The antibodies useful for diagnostic purposes may be prepared in the same manner as those described above for therapeutics. Diagnostic assays for PROPHO include methods which utilize the antibody and a label to detect PROPHO in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PROPHO are known in the art and provide a basis for diagnosing altered or abnormal levels of PROPHO expression. Normal or standard values for PROPHO expression are established by combining body fluids or cell extracts taken from normal mammalian subjects, preferably human, with antibody to PROPHO under conditions suitable for complex formation The amount of standard complex formation may be quantified by various methods, but preferably by photometric, means. Quantities of PROPHO expressed in subject, control and disease, samples from biopsied tissues are compared with the standard values.

Deviation between standard and subject values establishes the parameters for diagnosing disease.

In another embodiment of the invention, the polynucleotides encoding PROPHO may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PROPHO may be correlated with disease. The diagnostic assay may be used to distinguish between absence, presence, and excess expression of PROPHO, and to monitor regulation of PROPHO levels during therapeutic intervention.

In one aspect, hybridization with PCR probes which are capable of detecting polynucleotide sequences, including genomic sequences, encoding PROPHO or closely related molecules, may be used to identify nucleic acid sequences which encode PROPHO. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PROPHO, alleles, or related sequences.

Probes may also be used for the detection of related sequences, and should preferably contain at least 50% of the nucleotides from any of the PROPHO encoding sequences. The hybridization probes of the subject invention may be DNA or RNA and derived from the nucleotide sequence of SEQ ID NO:2 or from genomic sequence including promoter, enhancer elements, and introns of the naturally occurring PROPHO.

Means for producing specific hybridization probes for DNAs encoding PROPHO include the cloning of nucleic acid sequences encoding PROPHO or PROPHO derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding PROPHO may be used for the diagnosis of conditions, disorders, or diseases which are associated with expression of PROPHO. Examples of such disorders include: various types of cancer such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders associated with inflammation such as Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and disorders associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding PROPHO may be used in Southern or northern analysis, dot blot, or other membrane-based technologies; in PCR technologies; or in dipstick, pin, ELISA assays or microarrays utilizing fluids or tissues from patient biopsies to detect altered PROPHO expression. Such qualitative or quantitative methods are well known in the art.

In a particular aspect, the nucleotide sequences encoding PROPHO may be useful in assays that detect activation or induction of various cancers, particularly those mentioned above. The nucleotide sequences encoding PROPHO may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PROPHO in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PROPHO, a normal or standard profile for expression is established. This may be accomplished by combining body fluids or cell extracts taken from normal subjects, either animal or human, with a sequence, or a fragment thereof, which encodes PROPHO, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PROPHO may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PROPHO include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides derived from any of the polynucleotide sequences described herein may be used as probes in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the fall length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode PROPHO may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding PROPHO on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PROPHO, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PROPHO and the agent being tested, may be measured.

Another technique for drug screening which may be used provides for high throughput screening of compounds having suitable binding affinity to the protein of interest as described in published PCT application WO84/03564. In this method, as applied to PROPHO large numbers of different small test compounds are synthesized on a solid substrate, such as plastic pins or some other surface. The test compounds are reacted with PROPHO, or fragments thereof, and washed. Bound PROPHO is then detected by methods well known in the art. Purified PROPHO can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PROPHO specifically compete with a test compound for binding PROPHO. In this manner, the antibodies can be used to detect the presence of any peptide which shares one or more antigenic determinants with PROPHO.

In additional embodiments, the nucleotide sequences which encode PROPHO may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I THP1PLB01 cDNA Library Construction

The THP1PLB01 cDNA library was custom-constructed from activated human monocytes by Stratagene (Stratagene, La Jolla, Calif.). Poly(A+)RNA was purified from THP-1 cells which were cultured for 48 hr with 100 nm TPA and activated with 1 µg/ml LPS after 4 hr. cDNA synthesis was primed separately with both oligo d(T) and random hexamers and the two cDNA libraries were treated separately. Synthetic adaptor oligonucleotides were ligated onto cDNA ends enabling insertion into UNI-ZAP™ vector system (Stratagene). Finally, the two libraries were combined into a single library by mixing equal numbers of bacteriophage.

The cDNA library can be screened with either DNA probes or antibody probes and the PBLUESCRIPT phagemid (Stratagene) can be rapidly excised in vivo. The custom-constructed library phage particles were transfected into E. coli host strain XL1-BLUE (Stratagene). Alternative unidirectional vectors include but are not limited to PCD-NAI (Invitrogen, San Diego, Calif.) and PSH1OX-1 (Novagen, Madison, Wis.).

II Isolation and Sequencing of cDNA Clones

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT plasmid and the cDNA insert. The phagemid DNA was secreted from the cells, purified, and used to re-infect fresh host cells, where the double stranded phagemid DNA was produced. Because the phagemid carries the gene for β-lactamase, the newly-transformed bacteria are selected on medium containing ampicillin.

Phagemid DNA was purified using the MAGIC MINI-PREPS DNA purification system (Promega catalogue #A7100; Promega, Madison, Wis.). The DNA was eluted from the purification resin already prepared for DNA sequencing and other analytical manipulations. Phagemid DNA was also purified using the QIAWELL-8 plasmid, QIAWELL PLUS, and QIAWELL ULTRA DNA purification system (QIAGEN, Chatsworth, Calif.). The DNA was eluted from the purification resin already prepared for DNA sequencing and other analytical manipulations.

The cDNA inserts from random isolates were sequenced in part. Conventional enzymatic methods employ DNA polymerase Klenow fragment, SEQUENASE or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labelled precursors) or by fluorescence (for fluorescent-labelled precursors). Recent improvements in mechanized reaction preparation, sequencing and analysis using the fluorescent detection method have permitted expansion in the number of sequences that can be determined per day (such as the Applied Biosystems 373 DNA sequencer and CATALYST 800).

III Homology Searching of cDNA Clones and Their Deduced Proteins

Using the nucleotide sequences derived from the cDNA clones as query sequences (the sequences of the Sequence Listing), databases containing previously identified sequences are searched for areas of homology (similarity). Such databases include Genbank and EMBL. Two homology search algorithms were used. Homology algorithms help identify identical as well as only related sequences.

The first algorithm was originally developed by D. J. Lipman and W. R. Pearson, "Rapid and Sensitive Protein Similarity Searches", (1985) Science 227: 1435. In this algorithm, the homologous regions are searched in a two step manner. In the first step, the highest homologous regions are determined by calculating a matching score using a homology score table. The parameter 'Ktup' is used in this step to establish the minimum window size to be shifted for comparing two sequences. Ktup also sets the number of bases that must match to extract the highest homologous region among the sequences. In this step, no insertions or deletions are applied and the homology is displayed as an initial (INIT) value.

In the second step, the homologous regions are aligned to obtain the highest matching score by inserting a gap in order to add a probable deleted portion. The matching score obtained in the first step is recalculated using the homology score Table and the insertion score Table to an optimized (OPT) value in the final output.

DNA homologies between two sequences can be examined graphically using the Harr method of constructing dot matrix homology plots (Needleman, S. B. and Wunsch, C. O. (1970) J. Mol. Biol 48:443). This method produces a two-dimensional plot which can be useful in determining regions of homology versus regions of repetition.

The second algorithm was developed by Applied Biosystems Inc. and has been incorporated into the INHERIT 670 sequence analysis system. In this algorithm, Pattern Specification Language (developed by TRW Inc.) is used to determine regions of homology. There are three parameters that determine how the sequence comparisons are run: window size, window offset, and error tolerance. Using a combination of these three parameters, the DNA database is searched for sequences containing regions of homology and the appropriate sequences are scored with an initial value. Subsequently, these homologous regions are examined using dot matrix homology plots to determine regions of homology versus regions of repetition. Smith-Waterman alignments were used to display the results of the homology search.

Following the search for homologous regions, the sequences from the cDNA clones were classified as to whether they are exact matches (regions of exact homology) homologous human matches (regions of high similarity, but not exact matches), homologous non-human matches (regions of high similarity present in species other than human), or nonmatches (no significant regions of homology to previously identified nucleotide sequences).

Searches of the deduced polypeptides and peptides are done in a manner analogous to that done with the cDNA sequences. The sequence of the polypeptide is used as a query sequence and compared to the previously identified sequences contained in a database such as Swiss/Prot or the NBRF Protein database to find homologous polypeptides. These polypeptides are initially scored for homology using a homology score table (Orcutt, B. C. and Dayhoff, M. O. Scoring Matrices, PIR Report MAT-0285 (February 1985)) resulting in an INIT score. The homologous regions are aligned to obtain the highest matching scores by inserting a gap which adds a probable deleted portion. The matching score is recalculated using the homology score Table and the insertion score Table resulting in an optimized (OPT) score. Even in the absence of knowledge of the proper reading frame of an isolated sequence, the above-described polypeptide homology search may be performed by searching all 3 reading frames.

Peptide and protein sequence homologies can also be ascertained using the INHERIT 670 sequence analysis system in an analogous way to that used in DNA sequence homologies. Pattern specification language and parameter windows are used to search polypeptide databases for sequences containing regions of homology which are scored with an initial value. Subsequent examination with a dot-matrix homology plot determines regions of homology versus regions of repetition.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ® database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PROPHO occurs. Abundance and percent abundance are also reported. Abundance directly reflects the number of times a particular transcript is represented in a cDNA library, and percent abundance is abundance divided by the total number of sequences examined in the cDNA library.

V Extension of PROPHO Encoding Polynucleotides

The nucleic acid sequence of the Incyte Clone 13177 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| Step 1 | 94° C. for 1 min (initial denaturation) |
| --- | --- |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA gel purification kit (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 μCi of [γ-$^{32}$P] adenosine triphosphate (Amersham) and T4 polynucleotide kinase is (DuPont NEN®, Boston, Mass.). The labeled oligonucleotides are substantially purified with Sephadex G-25 superfine resin column (Pharmacia & Upjohn). An aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots, or in the alternative, blots are exposed to in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the PROPHO-encoding sequence, or any part thereof, is used to decrease or inhibit expression of naturally occurring PROPHO. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of PROPHO, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PROPHO-encoding transcript.

IX Expression of PROPHO

Expression of PROPHO is accomplished by subcloning the cDNAs into appropriate vectors and transforming the vectors into host cells. In this case, the cloning vector is also used to express PROPHO in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of PROPHO into the bacterial growth media which can be used directly in the following assay for activity.

X Demonstration of PROPHO Activity

PROPHO can be expressed by transforming a mammalian cell line such as COS7, HeLa or CHO with an eukaryotic expression vector encoding PROPHO. Eukaryotic expression vectors are commercially available, and the techniques to introduce them into cells are well known to those skilled in the art. The cells are incubated for 48–72 hours after transformation under conditions appropriate for the cell line to allow expression of PROPHO. Then, phase microscopy is used to compare the mitotic index of transformed versus control cells. A decrease in the mitotic index indicates PROPHO activity.

XI Production of PROPHO Specific Antibodies

PROPHO that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems peptide synthesizer model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra).

Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring PROPHO Using Specific Antibodies

Naturally occurring or recombinant PROPHO is substantially purified by immunoaffinity chromatography using antibodies specific for PROPHO. An immunoaffinity column is constructed by covalently coupling PROPHO antibody to an activated chromatographic resin, such as CnBr-activated Sepharose (Pharmacia & Upjohn). After the coupling, the resin is blocked and washed according to the manufacturer's instructions.

Media containing PROPHO is passed over the immunoaffinity column, and the column is washed under conditions that allow the preferential absorbance of PROPHO (e.g., high ionic strength buffers in the presence of detergent). The column is eluted under conditions that disrupt antibody/PROPHO binding (eg, a buffer of pH 2–3 or a high concentration of a chaotrope, such as urea or thiocyanate ion), and PROPHO is collected.

XIII Identification of Molecules Which Interact with PROPHO

PROPHO or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled PROPHO, washed and any wells with labeled PROPHO complex are assayed. Data obtained using different concentrations of PROPHO are used to calculate values for the number, affinity, and association of PROPHO with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding a humane protien phosphatase comprising the amino acid sequence of SEQ ID NO: 1 or enzymatically active fragments thereof.

2. A polynucleotide sequence which hybridizes under stringent conditions to the polynucleotide sequence of claim 1.

3. A composition comprising the polynucleotide sequence of claim 2.

4. An isolated and purified polynucleotide sequence comprising SEQ ID NO:2.

5. A composition comprising the polynucleotide sequence of claim 4.

6. A polynucleotide sequence which is complementary to the polynucleotide sequence of claim 2.

7. A composition comprising the polynucleotide sequence of claim 6.

8. An expression vector containing of the polynucleotide sequence of claim 2.

9. A host cell containing the vector of claim 8.

10. A method for producing a polypeptide comprising the amino acid sequence of SEQ ID NO:1, or enzymatically active fragments thereof, the method comprising the steps of:
    a) culturing the host cell of claim 10 under conditions suitable for the expression of the polypeptide; and
    b) recovering the polypeptide from the host cell culture.

11. A method for detecting a polynucleotide which encodes a human protein phosphatase in a biological sample comprising the steps of:
    a) hybridizing the polynucleotide of claim 6 to nucleic acid material of a biological sample, thereby forming a hybridization complex; and
    b) detecting said hybridization complex, wherein the presence of said complex correlates with the presence of a polynucleotide encoding the human protein phosphatase in said biological sample.

* * * * *

UNITED STATES PATENT AND TRADEMARK OFFICE
CERTIFICATE OF CORRECTION

PATENT NO. : 5,853,997
DATED : December 29, 1998
INVENTOR(S) : Bandman et al.

It is certified that error appears in the above-identified patent and that said Letters Patent is hereby corrected as shown below:

Col. 45, line 51, delete "humane" and insert --human--.
Col. 45, line 51, delete "protien" and insert --protein--.
Col. 45, line 58, delete "claim 2" and insert --claim 1--.
Col. 45, line 64, delete "claim 2" and insert --claim 1--.
Col. 45, line 68, delete "claim 2" and insert --claim 1--.
Col. 46, line 54, delete "claim 10" and insert --claim 9--.

Signed and Sealed this
First Day of February, 2000

Attest:

Attesting Officer

Q. TODD DICKINSON
Acting Commissioner of Patents and Trademarks